United States Patent [19]
Hartong et al.

[11] 3,995,483
[45] Dec. 7, 1976

[54] METHOD FOR MAKING VISIBLE DEFECTS IN SURFACES

[75] Inventors: Antoon Th. A. Hartong, Delft; Gerriet H. Douma, Bergambacht, both of Netherlands

[73] Assignee: Nederlandse Organisatie voor Toegepast-Natuurwetenschappelijk Onderzoek ten behoeve van Nijverheid, Handel en Verkeer, The Hague, Netherlands

[22] Filed: Aug. 19, 1975

[21] Appl. No.: 605,876

[30] Foreign Application Priority Data
Aug. 23, 1974 Netherlands ............... 7411251

[52] U.S. Cl. ..................... 73/104; 252/301.19; 252/408
[51] Int. Cl.² ........................ G01N 19/08
[58] Field of Search ........... 73/104; 252/301.2 P, 252/408

[56] References Cited
UNITED STATES PATENTS

| 2,806,959 | 9/1957 | De Forest et al. | 73/104 X |
| 3,184,596 | 5/1965 | Alburger | 252/301.2 P X |
| 3,279,243 | 10/1966 | Molina | 73/104 |
| 3,715,227 | 2/1973 | Alburger | 252/301.2 P X |

Primary Examiner—Richard C. Queisser
Assistant Examiner—John P. Beauchamp
Attorney, Agent, or Firm—Spencer & Kaye

[57] ABSTRACT

A method and a device for making visible defects in surfaces, in particular hot surfaces, by applying to the surface a penetrating liquid comprising a dye that soaks in the defects, removing the excess of liquid, applying on to the surface a developer such as a synthetic resin, which, after the dye from the defects has migrated into the former, is cured by the heat content of the surfaces into a replica of the surface in which the reversed image of the defects has been recorded and a replica made according to the method.

18 Claims, 2 Drawing Figures

METHOD FOR MAKING VISIBLE DEFECTS IN SURFACES

BACKGROUND OF THE INVENTION

The invention relates to a method for making visible defects in surfaces and to a device for the application of this method.

DESCRIPTION OF THE PRIOR ART

It is known in the art to apply to a surface, of which it is suspected that defects such as cracks or pores occur in it, a penetrating liquid that comprises a dye that soakes in the defects, to wipe away the excess of liquid and then apply to the surface a layer of developer, into which the dye remained in the defects migrates and thus brings the defects to light.

This generally known method has the drawback that in the case too much developer has been applied the defects are badly visible because the migration through the developer proceeds too slowly and the dye does not come sufficiently to the surface of the developer, so that a number of small defects do not come to light, whereas if too little developer has been applied and the dye bleeds through too far, small defects are taken for great defects. It requires a certain skill to obtain the correct balance.

Besides, there is the drawback that when the developer with the dye once has been removed from the surface, the defects cannot be retrieved, unless photos have been taken from them. The latter can be realized rather easily when tracing defects in simple surfaces, but when it regards an investigation of a complicated surface, such as the inner and outer surfaces of small tubes, taking photos requires a special technique.

SUMMARY OF THE INVENTION

It is the object of the invention to provide a method in which these drawbacks have been removed and moreover, the advantage occurs that a preservable replica of the surfaces investigated is obtained.

Therefore, according to the invention, after removal of the excess of penetrating liquid, on to the surface a layer of synthetic resin is applied that, after the dye from the defects has migrated into it, is cured into a replica of the surface concerned.

The method is preferably applied for evaluating welded seams, after applying the penetrating liquid and removal of the excess of it, according to the invention the synthetic resin being cured by the heat of the welded piece of work. As a result, immediately after welding a reversed image of the weld is obtained, which in form and colour indicates the locations of the defects. Prompt action can be taken to repair the defects, while in the replica the locations and the natures of the defects remain preserved.

Whereas in the methods known in the art with penetrating liquids red dyes are preferred, in the methods according to the invention, preferably, use is made of blue or green dyes, which show a more restricted migration into the synthetic resin, but for a permanent registration have a greater light-fastness. Preferably, use is made of dyes that belong to the anthraquinone and/or phthalocyanine dyes, which are solved in alcohols, glycols, acetates and/or ketones to a high-grade penetrating liquid with a dye concentration of 1–100 gms. p. liter solvent.

Preferably, as synthetic resin a dispersion of pvc with maximum 15% polyvinylacitate particles in plasticizers or mixtures thereof is applied, to which fillers, stabilizers and viscosity-reducing compounds and/or pigments may have been added. The dispersion of pvc particles, preferably, contains 5 to 10% polyvinylacetate.

Furthermore, as synthetic resin copolymer systems are applicable that can be applied as a thick liquid or paste, such as thermohardening polyesters, linear polyols and isocyanates, natural and synthetic rubbers, such as polyurethane rubbers and silicon rubbers, monomers that locally polymerize under the influence of heat and of a catalyst, such as methylmethacrylate, styrene, whether or not with thickening agents.

BRIEF DESCRIPTION OF THE DRAWING

The invention is further described hereinafter and elucidated with reference to a drawing.

DESCRIPTION OF THE PREFERRED EMBODIMENTS

Figure 1:
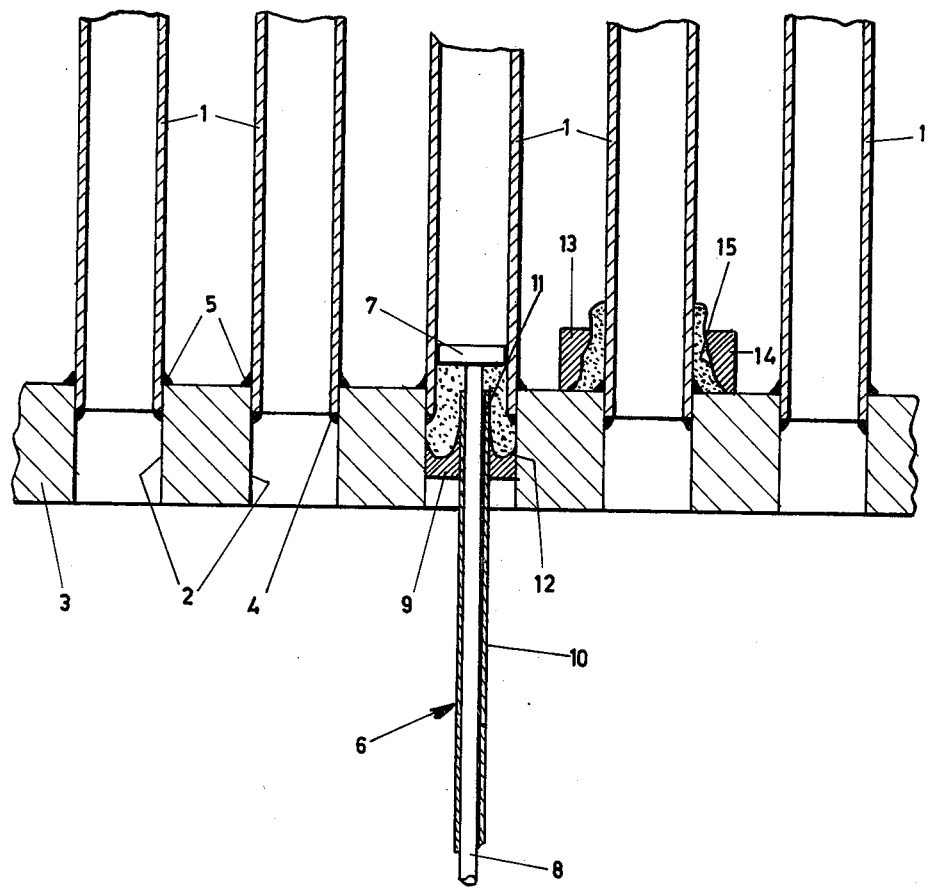
FIG. 1 shows a tube-plate with welded-in tubes, for controlling the welds two embodiments being given of devices for implementing the method according to the invention.

According to FIG. 1 a number of tubes 1 are welded in bores 2 of a tube-plate 3 with internal circular welded seams 4 and external circular welded seams 5.

So as to control internal welded seams 4 an auxiliary tool 6 is applied, which consists of a disc 7 on a rod 8 and a support 9, which is mounted on to a tube 10 slidable over rod 8. Support 9 has a central tappet 11 and at the periphery two or more cams 12.

So as to control external welded seams 5 an auxiliary tool is applied that comprises two half rings 13 and 14 as supports each with a cavity 15, which around tube 1 are laid abuttingly against each other and bear on tube-plate 3.

These auxiliary tools are applied in the method described hereinafter.

When into a tube-plate 3 a row of tubes 1 has been welded and the welds are still hot, on to the welds and their surroundings a dyed penetrating liquid is applied. The latter contains a blue or green dye, belonging to the "solvent blues" or "solvent greens", occurring in the Colour index and chemically belonging to the anthraquinone and/or phthalocyanine dyes, in a solvent such as ethyl alcohol, acetone, methyl ethyl ketone, ethyl acetate, methyl glycol, toluene or similar agents, which belong to the group of alcohols, glycols, acetates and ketones. The concentration of the dyes amounts to 1–100 gms. per liter solvent and to the agent an equal volume of a colourless penetrant is added, which contains paraffin or similar products as well as approximately 1/10 part of a concentrated synthetic soap solution.

The composed penetrating liquid is applied in excess to the surfaces when these still have a temperature of 100° to 160° C. The excess of liquid is removed with wet cloths or wipers and the remaining liquid is allowed to act on the surface for 2 to 5 minutes, the dye penetrating into pores or cracks present.

Then the surfaces are wetted with an emulsion containing a silicone fat, so as to prevent the adhesion of the synthetic resin paste that will be applied later. Then the welds and their surroundings are still at a temperature above 100° C. If the temperature has become too low, with means known in the art, the location of the weld or the surface can be heated to the temperature desired i.e. above 100° C.

Finally, at the locations to be investigated a synthetic resin paste is applied, which consists of a dispersion of polyvinyl chloride, whether or not with polyvinylacetate particles in plasticizers or mixtures thereof, to which fillers such as chalk, barytes, dye pigments and the like may have been added, as well as stabilizers and compounds that affect the viscosity. Maximum 15% polyvinylacetate may have been added. A percentage of 5–10% polyvinylacetate is preferred. Also as a thick liquid or paste, copolymers can be used of thermohardening polyesters, linear polyols and isocyanates, natural rubbers and synthetic rubbers, monomers that polymerize locally under the influence of heat and of a catalyst, such as methyl methacrylate, styrene and the like, whether or not with thickening agents.

As plasticizers can be used various phthalates, such as dibutyl phthalate, benzyl butyl phthalate or phosphoric acid-like esters such as tricresolphosphate, aliphatic plasticizers and the like, whereas as stabilizers are added compounds of metal with fatty acids, so as to prevent the decomposition of the synthetic resin dispersion at high temperatures. The pastes may have been pregelated at 70° C to a thickening acceptable to the eye and then they are applied to the locations desired.

Preferably, a synthetic resin paste is applied consisting of 100 parts of pvc (Solvic 340), 55 to 70 parts of di-2-ethyl hexylphthalate (DOP), 2 parts of heatstabilizer based on Cd/Ba (Flomax 25), 1 part of polyethylene glycol (400)-mono-oleate (Pegmo 400) and 0 to 2 parts of Titan white (Kronos Cl 220). The synthetic resin paste with 55 parts (DOP) hereby gave the best results. For internal welds 4 on to support 9 an amount of synthetic resin paste is applied in excess and tool 6 is inserted into a bore 2 of tube-plate 3 so far that cams 12 butt against a constriction formed by welded seam 4. Then rod 8 is moved in respect of tube 10, so that disc 7, which reaches into the interior of the tube, is drawn to support 9 and the synthetic resin paste is compressed so far that it is completely pressed against the wall and adopts the contours of welded seam 4 and the direct environment of it, because it melts as a result of the heat of the metal tube and tube-plate. Then the synthetic resin paste cures for 2 to 5 minutes. In the meantime, however, the dye that had remained in the pores or the cracks has migrated locally into the synthetic resin paste. There is no unlimited migration as a result of which the dye might spread into the whole mass of synthetic resin and the pattern of the defects might get lost, because the synthetic resin is cured through the heat that is fed from the tube and the tube-plate. Consequently, the so-called bleeding of the dye is practically impossible. The cured plug of synthetic resin is a replica of the macroscopic design of the weld and its environment and shows a complete reversed image in colour of the defects. It has been found that even of small cracks of 0.5 micron width and 10 micron depth individual pictures are obtained.

Figure 2:
FIG. 2 shows a replica manufactured according to the method.

When the dye has been absorbed and the synthetic resin has cured for the greater part, the plug that has obtained a shape such as has been shown in FIG. 2, is lifted with the tool and loosened from it. The it may be further fixed by heating it in a hot place, such as in a furnace, for another 5 to 15 minutes at a temperature of approximately 150° C. In so doing, further migration of the dye into the plug is excluded and the replica of the weld can be preserved with the reversed image of the defects found and the exact location of them.

If the defects were of such a nature that the weld had to be rejected, then it can be chipped out or drilled away and be replaced by a new weld. Of the latter is made a replica again, so that also the repairing actions have been recorded and can be entered in a register, if desired.

For external welded seams 5 the auxiliary tool is used that consists of two half rings 13 and 14 as support. In cavity 15 of those two half rings an amount of the previously mentioned synthetic resin paste is applied and it is brought in the correct place by compressing the half rings around a tube 1 and against tube-plate 3. By the heat of the latter the paste melts and the excess is pressed away at the top of the ring. The paste absorbs the dye from the cracks or pores, if any, and is cured by the own heat of the tube and the tube-plate.

The synthetic resin ring obtained, after some minutes, with a small knife is cut through between the separation of the half rings and then can be released from the tube. After further fixing, if desired, for 5 to 15 minutes in a furnace at 150° C the half rings are ready and the weld and its environment can be evaluated with reference to the replica obtained.

The great advantage of the method according to the invention is that here from the newly welded tube and tube-plate that are still hot excellent replicas can be obtained with the direct reversed images of the defects in colour, which have been fixed by heat and can be evaluated directly. In case of customary methods photos are taken, if desired, of the pattern of the cracks, as this has penetrated in colour through the layer of developer and that can only be implemented when the welds have cooled down. Moreover, taking photos of internal welds is an activity for which special lenses, cameras and photographic materials must be used, whereas one must wait until the temperature of the places to be investigated allows for the insertion of the equipment and then the photos have to be developed, still. In so doing, the plane photos obtained of a stereometric object contain distortions that make the evaluation still more difficult.

With the method according to the invention can be worked immediately after welding and exactly the high temperature of the welded places is of advantage, because as a result of that the synthetic resin replicas are cured. It mus be aimed at, though, that the temperatures is not too high, because otherwise the synthetic resin cures too quickly and not an accurate reversed image of the surface is obtained.

Therefore, the temperature will preferably have to be not higher than 160° C for the pvc paste used in the Example. For the other synthetic resins adapted temperatures can be taken, that preferably are above 100° C, so that moisture does not cause any trouble.

We claim:
1. A method for making visible defects in a hot surface having a temperature of above 100° C comprising:
    applying to the hot surface, a penetrating liquid containing a dye that soaks in the defects;
    removing excess penetrating liquid from the hot surface;
    applying, as a developer, a layer of a heatcurable synthetic resin paste to the hot surface after removal of the excess penetrating liquid, said dye migrating into said layer from the defects;

curing the synthetic resin by the heat content of the hot surface into a replica of the surface in which the reversed image of the defects is recorded; and removing the replica from the hot surface to preserve the location and nature of the defects.

2. A method according to claim 1, wherein the synthetic resin is applied as a paste that comprises a dispersion of pvc, with maximum 15% polyvinylacetate particles, in a plasticizer.

3. A method according to claim 2, wherein the paste contains a filler.

4. A method according to claim 2, wherein said synthetic resin paste consists of 100 parts of pvc, 55 to 70 parts to di-ethyl-hexyl phthalate, 2 parts of a heat stabilizer based on Cd/Ba, 1 part of polyethylene glycol(400)-mono-oleate and 0 to 2 parts of Titan white.

5. A method according to claim 1, wherein the dye in the penetrating liquid comprises a "solvent blue" or "solvent green" of the Colour index and is at least one compound which belongs to the anthraquinon or phthalocyanine dyes, said dye being present in the penetrating liquid in a solvent selected from the group of alcohols, glycols, acetates and ketones and in a concentration of 1 to 100 gms per liter of solvent.

6. The method according to claim 1, wherein the hot surface is a newly welded seam and the penetrating liquid and heat-curable resin are applied to a still hot surface resulting from the welding operation.

7. The method according to claim 1, wherein a tube contains the hot surface.

8. The method according to claim 1, wherein the tube contains an internal circular welded seam as the hot surface.

9. The method according to claim 1, wherein the tube contains an external circular welded seam as the hot surface.

10. The method according to claim 1, wherein the tube contains an internal circular welded seam and an external circular welded seam as hot surfaces.

11. The method according to claim 1, wherein the curing of the synthetic resin prevents unlimited migration of the dye.

12. The method according to claim 1, including further curing the synthetic resin after removal of the replica from the hot surface.

13. The method according to claim 1, including heating the hot surface after application of the penetrating liquid to bring the hot surface to a temperature above 100° C.

14. The method according to claim 1, wherein the synthetic resin is applied to the hot surface by pressing the resin against the hot surface, and the synthetic resin adopts the contours of the hot surface by melting.

15. A replica made according to the method of claim 1.

16. A method according to claim 2, wherein the paste contains a stabilizer.

17. A method according to claim 2, wherein the paste contains a compound which controls viscosity.

18. A method according to claim 2, wherein the paste contains a pigment.

* * * * *